United States Patent
McEwan et al.

(10) Patent No.: US 8,611,991 B2
(45) Date of Patent: Dec. 17, 2013

(54) SYSTEM AND METHOD FOR CONDUCTING MULTIPLEXED ELECTRICAL IMPEDANCE TOMOGRAPHY

(75) Inventors: Alistair Lee McEwan, Lewisham (AU); David Simon Holder, London (GB); Andre van Schaik, Blackheath (AU); Jonathan Craig Tapson, Cape Town (ZA)

(73) Assignees: The University of Cape Town, Cape Town (ZA); The University of Sydney, Sydney, NSW (AU)

( * ) Notice: Subject to any disclaimer, the term of this patent is extended or adjusted under 35 U.S.C. 154(b) by 552 days.

(21) Appl. No.: 12/744,734

(22) PCT Filed: Nov. 25, 2008

(86) PCT No.: PCT/IB2008/003208
§ 371 (c)(1),
(2), (4) Date: May 26, 2010

(87) PCT Pub. No.: WO2009/068961
PCT Pub. Date: Jun. 4, 2009

(65) Prior Publication Data
US 2010/0303321 A1    Dec. 2, 2010

(30) Foreign Application Priority Data
Nov. 26, 2007   (GB) .................................. 0723045.1

(51) Int. Cl.
  *A61B 5/04*  (2006.01)
(52) U.S. Cl.
  USPC ............ 600/544; 600/545; 600/546; 600/547

(58) Field of Classification Search
USPC .................................. 600/544–547; 607/1, 2
See application file for complete search history.

(56) References Cited

U.S. PATENT DOCUMENTS

| | | | | |
|---|---|---|---|---|
| 4,094,307 | A * | 6/1978 | Young, Jr. | 600/544 |
| 4,486,835 | A * | 12/1984 | Bai et al. | 378/21 |
| 4,539,640 | A | 9/1985 | Fry et al. | |
| 5,919,142 | A * | 7/1999 | Boone et al. | 600/547 |
| 6,201,990 | B1 * | 3/2001 | Wexler et al. | 600/547 |
| 7,288,943 | B2 * | 10/2007 | Matthiessen et al. | 324/628 |
| 7,847,565 | B2 * | 12/2010 | Woo et al. | 324/692 |
| 2004/0201380 | A1 | 10/2004 | Zimmermann et al. | |
| 2010/0303321 | A1 * | 12/2010 | McEwan et al. | 382/131 |
| 2011/0301441 | A1 * | 12/2011 | Bandic et al. | 600/306 |

OTHER PUBLICATIONS

McEwan et al., "Electrode Circuits for Frequency- and Code-Division Multiplexed Impedance Tomography", Biomedical Circuits and Systems Conference, 2007, pp. 130-133, Biocas, IEEE, IEEE, Piscataway, NJ, USA.

(Continued)

*Primary Examiner* — Sean Dougherty
(74) *Attorney, Agent, or Firm* — The Webb Law Firm

(57) ABSTRACT

A method is provided for taking electrical impedance tomography measurements using multiple electrodes located at selected positions external to a volume of a subject body. Multiple orthogonal or near-orthogonal signals are introduced simultaneously by way of selected different electrodes and resultant predetermined responses (if any) at receiving electrodes are recorded or determined. The signals are encoded using the technique of code division multiplexing and received signals at each receiving electrode are cross-correlated with original signals to determine the contribution of each original signal to a composite received signal. The invention also relates to apparatus suitable for use in applying a method.

9 Claims, 3 Drawing Sheets

(56) References Cited

OTHER PUBLICATIONS

McEwan et al., "Design and Calibration of a Compact Multi-frequency EIT System for Acute Stroke Imaging", Physiol. Meas., 2006, pp. S199-S210.

Brown, "Medical Impedance Tomography and Process Impedance Tomography: A Brief Review", Measurement Science and Technology, 2001, pp. 991-996, vol. 12.

McEwan et al., "Wide-bandwidth, High Frame Rate Electrical Impedance Tomography/Spectroscopy—A Code Division Multiplexing (CDM) Approach", Proceedings of the 1st International Conference on Biomedical Electronics and Devices, 2008, pp. 196-203, vol. 2.

Kaatze et al., "Broadband Dielectric Spectrometry of Liquids and Biosystems", Measurement Science and Technology, 2006, pp. R17-R35, vol. 17(2).

J.J. Spilker Jr., "GPS Signal Structure and Theoretical Performance", 1994, Am. Inst. Aeronautics and Astronautics Inc., Washington, (1996).

* cited by examiner

SYSTEM AND METHOD FOR CONDUCTING MULTIPLEXED ELECTRICAL IMPEDANCE TOMOGRAPHY

FIELD OF THE INVENTION

This invention relates to a system and method for conducting multiplexed electrical impedance tomography for the purpose of generating images of the interior of a volume of a three-dimensional body by way of a series of electrodes applied to the outer surface thereof.

More particularly, but not exclusively, the invention is concerned with a system and method for conducting multiplexed electrical impedance tomography that is particularly suitable for application in medical imaging of regions of the human body, especially for diagnostic purposes.

BACKGROUND TO THE INVENTION

Electrical impedance tomography (EIT), in which a volume is probed non-invasively by injecting currents (or magnetic fields) and measuring the electrical potential or magnetic fields at the periphery, has been reported as being useful for physiological imaging for some three decades.

Its applicability in industrial situations, in which it is called "process tomography", was recognized in the early 1980's, leading to a considerable investment in research into hardware, software, and reconstruction algorithms. More recently, there has been a growing interest in obtaining material contrast in the images by discriminating on the basis of the frequency response of impedance; this is electrical impedance spectroscopy (EIS). The combination of the two methods is generally called electrical impedance tomography spectroscopy (EITS).

In the standard implementation of EIT, the complex impedance is measured in terms of resistance and capacitance. A ring of electrodes is placed around the volume to be imaged; a current is injected through a pair of the electrodes, and the resulting electrical potentials measured at all or many of the other of the multiple electrodes employed. The signals are separated into a resistive and a capacitive signal, either by measuring the complex impedance directly, or by using separate ohmic and capacitive electrodes.

If the frequency of the injected current is swept through a range, or stepped through a set of fixed frequencies, the spectral response may also be obtained. For this purpose excitation current is switched sequentially to different pairs of electrodes, and a series of data sets acquired sequentially. When all the desired combinations have been measured, a reconstruction algorithm is used to produce an approximation of the distribution of material within the image plane, based on its impedance (in EIT) or impedance spectrum (in EITS). The reconstruction of EITS images is an area of active research, and many different methods are available (See McEwan, A., Romsauerova, A., Yerworth, R., Horesh, L., Bayford, R., & Holder, D. (2006). Design and calibration of a compact multi-frequency EIT system for acute stroke imaging, Physiol. Meas., 27, S199-S210).

There are a number of standard patterns of excitation and measurement in EITS. The most commonplace is that adjacent pairs of electrodes are used to inject current, and potentials are measured at the other electrodes. Regardless of the pattern used, a single frame of EIT data requires a great many measurements (the adjacent-pair method requires $k=n\times(n-1)$ measurements for n electrodes); and this number must be multiplied by the number of frequency points required.

Taking a frame of EIT data using sequential measurements (so-called time-division multiplexed or TDM measurements) is slow, so that frame rates in excess of 100 frames/second are extremely difficult to achieve. Whilst optimization of the TDM process to a very high degree is reported to have achieved frame rates of up to 1000 frames/second, most laboratory and commercial systems operate at orders of magnitude slower than this. EITS systems are slower still, with frame rates of 13 seconds/frame being generally achievable with a frequency range of 20 Hz-128 kHz in present day systems.

A basic constraint in EITS frame rate is imposed by the lower limit of spectral bandwidth; for example, if the impedance at 20 Hz is required, the frame rate per second will be limited to 20/k, where k is the number of sequential measurements required per frame; and even this limit implies sampling only a single cycle of the lowest frequency per measurement, which is somewhat difficult to achieve in practice. Use in the past has thus been limited, for example to EIT imaging of fast electrical and slow blood flow related changes during functional activity and epilepsy. These applications have traditionally used time-division multiplexing (TDM) of a single current source to pairs of electrodes over say 258 electrode combinations.

A method which presents itself for increasing the frame rate is to simultaneously inject currents which are modulated to be mathematically orthogonal, so that their contributions to the potential at any electrode can be separated by demodulation. For example, if a current of frequency $f_1$ is injected at one pair of electrodes, and a current of frequency $f_2$ at a second pair, then the potential across a third pair of electrodes can be separated into a component due to $f_1$ and a component due to $f_2$ by synchronously demodulating with those frequencies. The complex components of impedance can be extracted by in-phase and quadrature synchronous demodulation. The process is referred to as frequency-division multiplexed (FDM EIT).

A number of problems are encountered in FDM EIT as a consequence of accommodating simultaneous current injection and voltage measurement on the same electrode. If the current and voltage form part of the same impedance calculation, this comprises a two-terminal impedance measurement; whereas it is generally considered that a four-terminal measurement is required to avoid the problem of inadvertently including the contact or terminal resistance in the specimen resistance. If the current and voltage form part of a separate calculation, then this problem is avoided.

A second issue is that the current through any terminal must be a sum of orthogonal component currents, and equal and opposite components must flow through some other terminal. Ensuring that the net current due to each component is zero is electronically complicated, and has not been attempted in any of the FDM EIT systems known to applicant. These systems have generally avoided these problems by using separate sets of current injection and voltage measurement electrodes, although this has the disadvantage that twice the number of electrodes are required to obtain the same resolution.

Zimmerman et al in US published patent application US2004/201380 propose the use of orthogonal signals, either discrete sine waves or coded binary signals, as a way to use plural excitation electrodes simultaneously. However, their main application is in geophysics in which the focus is on detecting aqueous or metallic objects in a composite earth body which have a constant conductivity difference relative to the background. As a result of this their intended use of the system is apparently confined to within a small frequency range, their example of 10 Hz-19.9 Hz being illustrative of this.

OBJECT OF THE INVENTION

It is an object of this invention to provide a system and method for conducting multiplexed electrical impedance tomography that enables images to be generated at a speed that is superior to that practically associated with commercial systems presently available and of which applicants are aware.

SUMMARY OF THE INVENTION

In accordance with one aspect of this invention there is provided a method of taking electrical impedance tomography measurements using multiple electrodes located at selected positions external to a volume of a subject body and wherein multiple orthogonal or near-orthogonal signals are introduced simultaneously by way of selected different electrodes and resultant predetermined responses (if any) at receiving electrodes are recorded or determined, the method being characterized in that the signals are encoded using the technique of code division multiplexing and received signals at each receiving electrode are cross-correlated with original signals to determine the contribution of each original signal to a composite received signal.

Further features of the invention provide for the signal, in each instance, to be a specific length sequence of pulses with each sequence coded with a channel-specific code; for the signals to assume the form of pseudorandom noise (PRN) sequences (bit sequences which appear to be random, but in fact are deterministically generated, usually by means of a modulo-addition of bits in a shift register) such as the known 1023-bit Gold codes; for the signals to be broad band codes embracing a wide frequency spectrum of from 10 Hz to 5 MHz, or even 10 MHz or more with a resolution of 10 Hz; and for the received signals to be asynchronously de-multiplexed and cross-correlated.

It is a particular feature of the invention that the subject body may be a part of the human body, and in particular but not exclusively, the human head in which instance the method can be used for creating tomographic images and spectra indicative of an aneurysm or a stroke.

The invention also provides a method of conducting electrical impedance tomography spectroscopy that includes the method of taking electrical impedance tomography measurements as defined above and processing them to produce a required spectrum.

In accordance with a second aspect of the invention there is provided apparatus for conducting a method as defined above comprising a signal generator for simultaneously producing a set of orthogonal or near orthogonal signal currents encoded using the technique of code division multiplexing, a set of EIT electrodes connected to apply the signal currents to a body being investigated and to receive compound signal currents applied by way of other electrodes, and computer means programmed to de-multiplex and cross-correlate received signals; process the signals and generate required EIT data or EITS data, or both, as the case may be.

Further features of the second aspect of the invention provide for transformer coupling to be interposed between a signal generator and each pair of electrodes associated with a particular signal current with a primary winding of each transformer being connected to be energised by the signal generator and a secondary winding of each transformer being connected in series with a resistor between the members of a pair of electrodes.

It is to be noted that the transformer coupling defined above is also considered by applicants to be capable of broader general application of electrical signals or currents to the human body and such broader application is intended to fall within the scope of this invention.

In order that the above and other features of the invention may be more fully understood examples of the different aspects of the invention will now be described with reference to the accompanying drawings.

DETAILED DESCRIPTION WITH REFERENCE TO THE DRAWINGS

Figure 1:
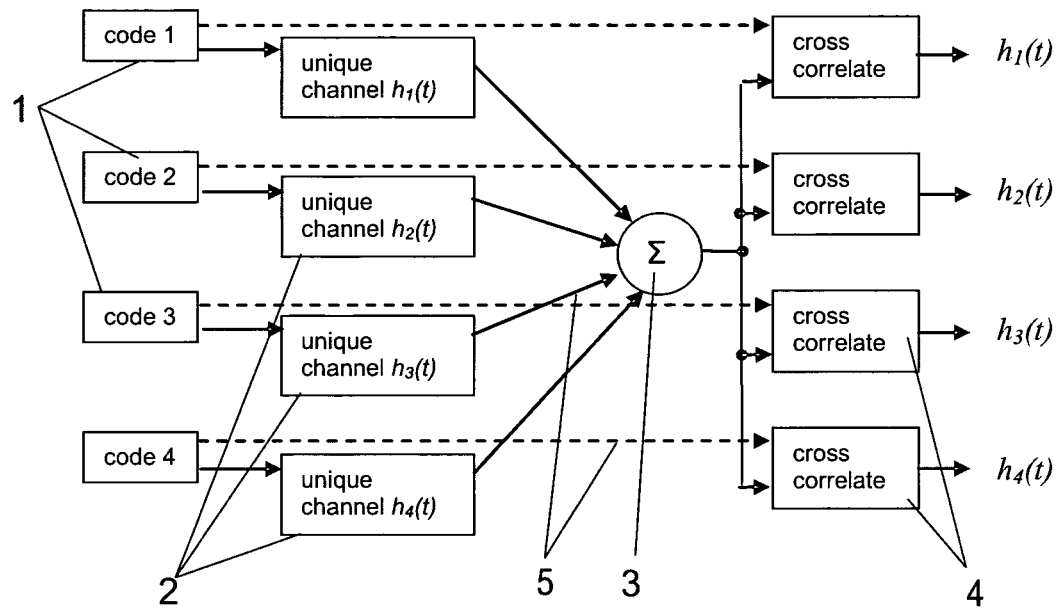
—
FIG. 1 shows a scheme of modulation and demodulation according to the invention.

The principle of code division multiplexing (CDM) is that the signal through a particular channel is modulated using a unique binary digital code to provide, in the instance illustrated in FIG. 1, four different channels that are differently coded in the manner indicated and that are indicated by numeral (1).

The basic requirements of the codes are that there should be at least one code per channel; that the codes should be orthogonal, or nearly so; and that the autocorrelation functions of the codes should be flat with a single sharp peak (in the ideal case, approximating a delta function).

Each resulting unique channel (2) in the measurement system is thus stimulated using a driving signal current modulated with a unique code. The channels are either deliberately or inadvertently mixed together as indicated by numeral (3).

At receivers that are indicated by numeral (4), the contribution due to each channel is recovered by cross-correlating the signal at the receiver using a copy (indicated by numeral (5)) of the original signal containing the channel's characteristic code. If the codes are orthogonal or near-orthogonal, there should be substantially complete separation of components.

Many different codes of binary or multi-level nature may be used and reference is made in particular to Gold codes as an example. These codes are bit sequences which appear to be random, but in fact are deterministically generated, usually by means of a modulo-addition of bits in a shift register. They are used commercially to carry time information in the Global Positioning System (GPS). Codes of this type are generally referred to as pseudorandom noise (PRN) sequences, as they appear to be random and have the characteristics of noise (Parkinson, B. W., & Spilker Jr., J. J. (1996). Global Positioning System: Theory and Applications, vol. 1, Am. Inst. Aeronautics and Astronautics Inc., Washington.). These codes have the property that their autocorrelation functions are extremely sharp, enabling them to be extracted from mixed, noisy signals at the receiver. The codes are inherently broadband signals, e.g. a 1 million length, pseudorandom code output at 10 Mbit/s would give the complete spectrum from 5 MHz-10 Hz with a resolution of 10 Hz. The acquisition time would be relatively fast at about 10 frames/second.

The use of CDM in the present application enables measurements to be taken over all the channels simultaneously. In addition, the spectral characteristics of the CDM input signal effectively interrogate the sample over a wide range of frequencies, and the output signals can be transformed to produce a spectrum, giving simultaneous wide-band spectroscopy on all channels.

More particularly, CDM enables orthogonal signal currents to be injected simultaneously, and the resulting potentials to be demodulated. This has an enormous advantage over FDM and TDM techniques, in that it is possible to sample at multiple frequencies simultaneously while sampling multiple physical channels. This enables wide-bandwidth multi-electrode spectroscopy to be performed in times equivalent to that taken for single measurements in present-day EITS systems.

It may be desirable to share electrodes between multiple measurement channels and a simple current injection arrangement at the electrode has thus been developed based on high-frequency transformers, which guarantees a net zero current flow for each orthogonal component.

An example of this is described in detail below for two dimensional imaging. It is, however, also applicable to three dimensional imaging. The resulting data is useful for imaging either the changes over time or frequency, or the absolute impedance of the object. In the following example a flat frequency spectrum is used, however this may easily be shaped to allow for medical safety standards.

Additionally the coded signals and electrode locations may be chosen to reduce the combined power of the signal at specific locations inside the object with a view to meeting safety standards or, for example, reduce the excitation of specific nerve fibers of the brain. This technique has wide application in medical imaging, new methods of electrical therapy (e.g. reversible and irreversible electroporation, trans-electrical stimulation and wound healing) and industrial process tomography (e.g. mining and oil transportation).

It is to be noted that a further advantage of utilising the system indicated above is the lower cost of producing and processing pulse based signals.

The traditional digital to analogue converter is not required; the signal source may be simpler as it controls only two (bipolar) amplitudes; and; instrumentation amplifier and analogue to digital converter requirements are relaxed. Demodulation is also simpler and cheaper to implement via cross-correlation. Patient-safe isolation and coupling may also be cheaper with the use of low cost pulse transformers described in more detail below. This technique allows fast EIT data acquisition over a wide bandwidth at a lower cost than alternatives. It is envisaged that the ability to use more electrodes quickly will lead to better images. It is anticipated that the present method may become the key method to prove the application of EIT to detecting acute stroke.

Reverting to the cross-correlation, a cross-correlation $R_{IO}$ between the unique input signals $I_n$ and the combined output signal $O_n$, may be calculated as follows:

$$R_{I_1 O}(m) = \frac{1}{N} \sum_{n=0}^{N-1} I_{1n} O_{n-m} \qquad (1)$$

where N is the epoch length of the PRN (nominally, 1023 bits, or the equivalent number of samples).

The output at any time k can be stated as the sum of the convolution of the impulse responses for the channels and the respective inputs as follows:

$$O_k = \sum_{i=0}^{k} I_{1i} h_{1(k-i)} + \sum_{i=0}^{k} I_{2i} h_{2(k-i)} + \sum_{i=0}^{k} I_{3i} h_{3(k-i)} + \ldots \qquad (2)$$

Substituting this into the cross-correlation, say for $I_1$ and the output:

$$R_{I_1 O}(m) = \frac{1}{N} \sum_{n=0}^{N-1} I_{1n} \left[ \sum_{i=0}^{n-m} I_{1i} h_{1(n-m-i)} + \sum_{i=0}^{n-m} I_{2i} h_{2(n-m-i)} + \sum_{i=0}^{n-m} I_{3i} h_{3(n-m-i)} + \ldots \right]$$

$$= \frac{1}{N} \sum_{n=0}^{N-1} I_{1n} \sum_{i=0}^{n-m} I_{1i} h_{1(n-m-i)} + \frac{1}{N} \sum_{n=0}^{N-1} I_{1n} \sum_{i=0}^{n-m} I_{2i} h_{2(n-m-i)} + \ldots$$

$$= \frac{1}{N} \sum_{n=0}^{N-1} \sum_{i=0}^{n-m} I_{1n} I_{1i} h_{1(n-m-i)} + \frac{1}{N} \sum_{n=0}^{N-1} \sum_{i=0}^{n-m} I_{1n} I_{2i} h_{2(n-m-i)} + \ldots \qquad (3)$$

On the basis that:

$$\sum_{i=0}^{k} I_{1i} h_{1(k-i)} = \sum_{i=0}^{k} I_{1(k-i)} h_{1k} \qquad (4)$$

Rearrangement provides the following:

$$R_{I_1 O}(m) = \frac{1}{N} \sum_{n=0}^{N-1} \sum_{i=0}^{n-m} I_{1n} I_{1(n-m-i)} h_{1i} + \frac{1}{N} \sum_{n=0}^{N-1} \sum_{i=0}^{n-m} I_{1n} I_{2(n-m-i)} h_{2i} + \ldots$$

$$= \sum_{i=0}^{n-m} R_{I_1 I_1}(m-i) h_{1i} + \sum_{i=0}^{n-m} R_{I_1 I_2}(m-i) h_{1i} + \ldots$$

$$= R_{I_1 I_i} * h_1$$

$$= h_1(m) \qquad (5)$$

The cross-correlation terms (those $R_{II}$ terms with non-identical indices for I) will sum to zero, because different Gold codes are effectively uncorrelated; so only the first correlation is non-zero. In continuous terms:

$$R_{I_1 O}(t) = R_{I_1 I_1}(t) * h_1(t) \qquad (6)$$

$$= \delta(t) * h_1(t)$$

$$= h_1(t)$$

The output of the cross-correlation is the impulse response of the channel, which represents the time-domain transform of the information we want.

PRN sequences having the appearance of noise and being like uniformly distributed white noise, have a spectrum that is flat within the limits of bandwidth. They are also delta-correlated; that is to say, their autocorrelation function consists of a Dirac delta function at the origin. This is the basis of their usefulness in demodulation, as shown above. From equation (6) above it will be seen that the input-output cross-correlation function of a channel in the system produces the transfer function h(t) of the channel. The Fourier transform of the cross-correlation function is as follows:

$$G(\omega) = \int_{-\infty}^{\infty} R_{I,O}(t) e^{-j\omega t} dt \qquad (7)$$
$$= \int_{-\infty}^{\infty} h(t) e^{-j\omega t} dt$$
$$= h(\omega)$$

The Fourier transform of the cross-correlation function thus produces the frequency response of the channel; which is to say, the complex spectrum of the channel impedance.

Figure 2:
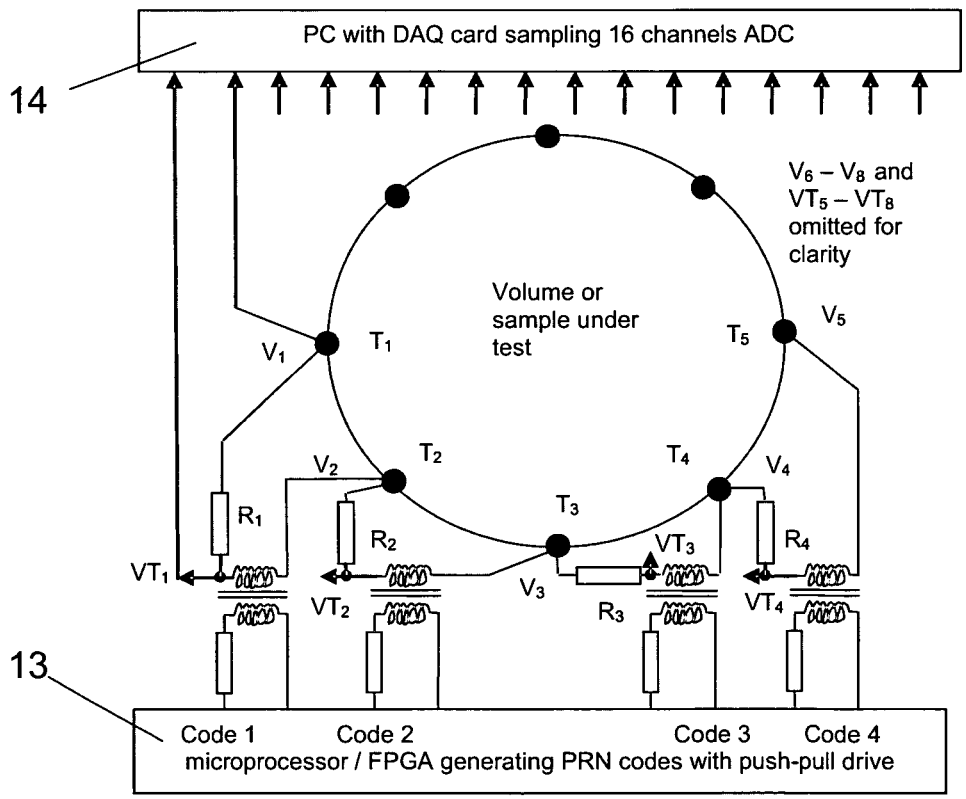
FIG. 2 shows a schematic block diagram of one embodiment of hardware that may be employed for implementing an application of the invention.

Turning now to the system hardware, and with reference to FIG. 2 (in which a number of elements are not shown in order to improve clarity), the system may comprise multiple EIT electrodes (10) at which injection and reception of signals is combined. Transformer coupling indicated by numeral (11) allows inflowing and outflowing currents due to each code to be exactly balanced, as well as providing isolation for safety. Transformer coupling of the drive currents to the EIT electrodes ensures matched source and sink currents. There is a resistor (12) in each transformer secondary, to allow direct measurement of the current in the secondary. The arrangement is as follows.

A signal generator (13) is provided for simultaneously producing a set of orthogonal or near orthogonal signal currents encoded using the technique of code division multiplexing in the form of Gold codes (using push-pull drive from two port pins, with a series resistor for current limiting). The sets of EIT electrodes are, in use, connected to apply the signal currents to a body being investigated and to receive compound signal currents applied by way of other electrodes. Each of the eight transformer secondaries is connected to a pair of electrodes, so that each electrode is connected to the high side of one secondary and the low side of another. Computer means (14) are provided that are programmed to de-multiplex and cross-correlate received signals using the principles described above to thereby process the signals and generate required EIT data or EITS data, or both, as the case may be.

In principle, the current between two terminals, say $T_1$ and $T_2$, should have a fixed amplitude, modulated in polarity by Code 1. In practice, this current is measured by sampling the voltage at the points $V_1$ and $VT_1$, and dividing the difference by the resistor value.

The impulse response for the voltage between $T_4$ and $T_5$, with respect to the current between $T_1$ and $T_2$, can then be calculated by cross-correlating the voltages ($V_1-VT_1$) and ($V_5-V_4$); and so on. The voltage across each ballast resistor gives the current due to that code (e.g. the current due to Code 3 is $I_3=(VT_3-V_3)/R_3$).

One possible problem that may be faced is that accurate impedance measurements often require a four-terminal approach, which traditionally requires the separation of current-injection and potential-measurement electrode pairs. If potential measurements are made on electrodes whilst current is being injected through them, the potential measured includes the voltage drop across the contact resistances, which is likely to be significant in most EIT applications.

Figure 3:
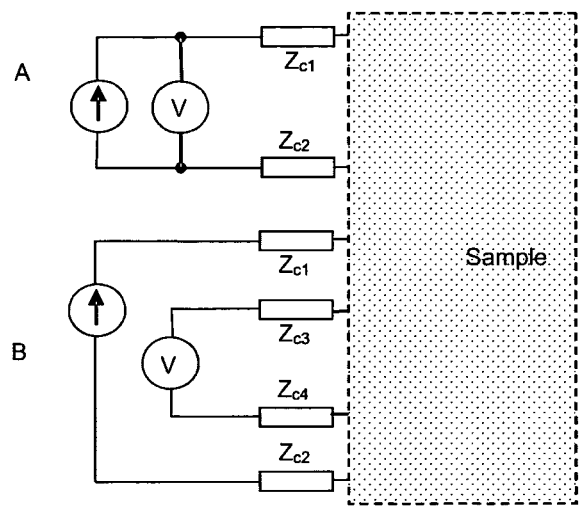
FIG. 3 shows schematically a comparison between a two-terminal and a four-terminal measurement.

This is shown schematically in FIG. 3 where a two-terminal arrangement is indicated by letter (A) and four-terminal arrangement is indicated by letter (B). In the former (A), the contact impedances $Z_{c1}$ and $Z_{c2}$ are inseparable from the sample impedance $Z_s$, so $V=I_s(Z_{c1}+Z_{c2}+Z_s)$. In the latter (B), however, the high input impedance of the voltmeter renders negligible the current through the contact resistances $Z_{c3}$ and $Z_{c4}$ so that $V=I_s Z_s$.

If the same electrodes are to be used simultaneously for current injection and voltage measurement in FDM and CDM systems, then the four-terminal method becomes difficult. One alternative is to use separate sets of electrodes for current injection and voltage measurement. This method was adopted in the FDM systems to date, as well as in some TDM systems. Unfortunately, this doubles the number of electrodes required for a given number of measurements. The reduced electrode size reduces the accuracy of the impedance measurement and increases the practical difficulties in wiring, mounting and isolating the electrodes.

The present invention thus provides a method and circuit whereby electrodes can simultaneously be used for current injection and voltage measurement, in CDM and FDM systems, while correctly implementing the four-terminal principle. Given any two orthogonal signals f(t) and g(t), it appears trivial to inject currents proportional to each and measure the induced voltages at some other point. The situation is complicated by the need for all terminals to act simultaneously in current injection, as shown conceptually in FIG. 4.

Figure 4:
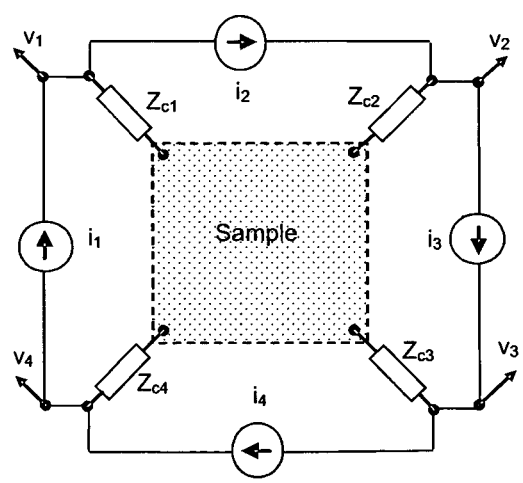
FIG. 4 illustrates schematically a problem of sharing electrodes amongst multiple, simultaneous current injection loops in a conventional arrangement; and,
FIG. 5 shows schematically an example of an arrangement of electrodes, current sources, transformers used for coupling the current sources to the electrodes, ballast resistors, and voltage measurement points, for four of a series of sixteen electrodes in one arrangement according to the second aspect of the invention.

It can be seen in FIG. 4 that the current sources are effectively connected in a ring. This illustrates the problem of sharing electrodes amongst multiple current injection loops, each injecting orthogonal current $i_n$. The voltage $v_n$ and impedance looking into each terminal (at the circuit side of the contact impedance $Z_{cn}$) is a complex function of the injected currents all around the outside loop. This places very stringent requirements on the sources; they must be "stiff" in the face of wide and unpredictable voltage and impedance fluctuations at their terminals; and given the complexity of orthogonal signals, they must be able to source and sink symmetrical (and bipolar) currents at high bandwidth. In practice, even with separate current injection and voltage measurement terminals, it has been found that current sources are seldom sufficiently stiff to render current measurement unnecessary.

Figure 5:
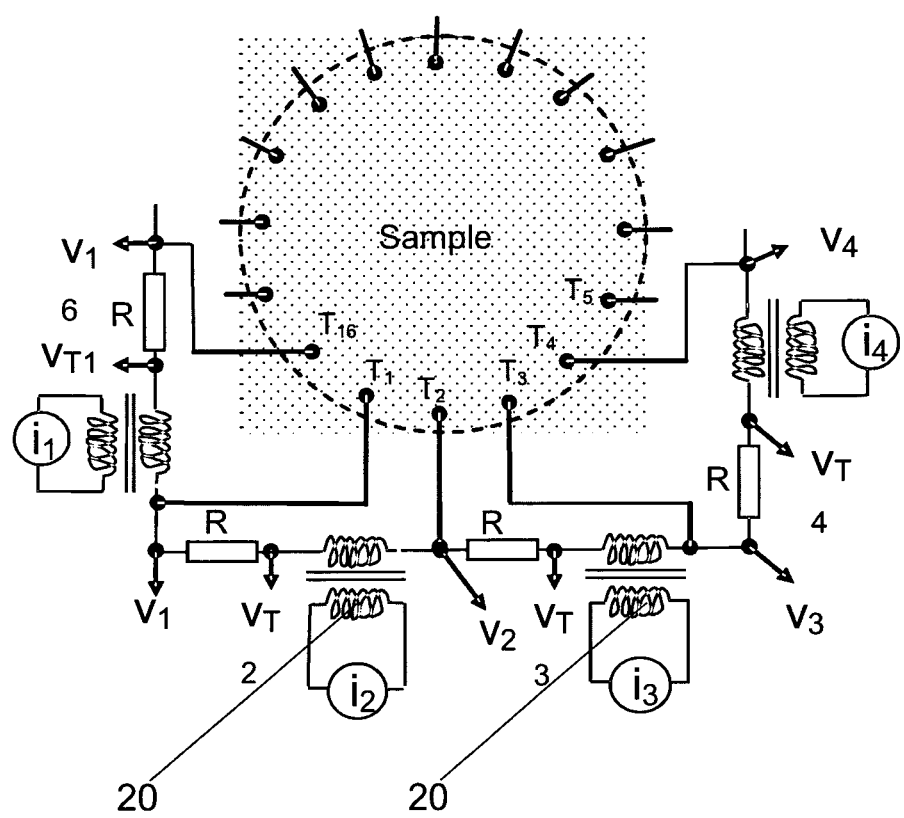

This invention thus provides for the use of high-frequency pulse transformers as current sources as a solution to the problem, as illustrated in FIG. 5. The circuit shown in FIG. 5 has current sources $i_n$, transformers (20), ballast resistors R, and voltage measurement points $v_n$. Such items are shown as being provided for four of the sixteen electrodes illustrated.

The simultaneous measurement may thus take place of the voltage $v_{3,4}$ induced between terminals $T_3$ and $T_4$ by the current $i_2$ injected between terminals $T_1$ and $T_2$; and the measurement of the voltage $v_{1,2}$ induced between terminals $T_1$ and $T_2$ by the current $i_4$ injected between terminals $T_3$ and $T_4$. The advantages of such transformers are that they source and sink symmetrical and bipolar currents without difficulty; and that they inherently provide galvanic isolation. By placing the small resistor R in series with each transformer, a compact circuit is provided in which the currents and induced voltages at 16 terminals can be measured using 32 single-ended ADC channels.

In the broader application, assume that $i_2$ is modulated by f(t) and $i_4$ is modulated by g(t), where f(t) and g(t) are orthogonal or nearly so, then for example in a FDM situation, $i_2$=If(t) and $i_4$=Ig(t) where f(t) and g(t) would be non-identical sinusoidal carrier waves and I is a constant. If the voltage measured at terminals k and j by the current injected by transformer m as $v_{k,j}|i_m$ then:

$$v_{1,2}|i_4=[(v_1-v_2)\times(vT_4-v_3)/R)]\text{LPF}$$

$$v_{3,4}|i_2=[(v_3-v_4)\times(vT_2-v_1)/R)]\text{LPF}$$

where [ ]LPF represents the low pass filtering of the expression in parentheses (this would be the standard synchronous demodulation algorithm for frequency-multiplexed signals). Other modulation and demodulation schemes can similarly use $(vT_m-v_n)/R$, where these are the two voltages measured either side of transformer m's series resistor, as a representation of the current injected for the purposes of demodulation.

It is in anticipated that this invention will be particularly useful in medical imaging and especially in imaging acute stroke as it could be employed for urgent neuroimaging where CT is not practical thereby enabling the use of clot-dissolving therapy. For stroke a system is required that operates over a broad bandwidth (10 Hz-10 MHz) and is faster (10 frames/s) to reduce noise and movement artefact.

In medical imaging for clinical use it is envisaged that apparatus provided by this invention could be sold as an addition to existing physiological (EEG/ECG, respiratory) monitors or anatomic medical imagers (xray-CT, MRI) to provide physiological information. Due to the low cost and safety it could also be sold for home use.

For industrial imaging it could be sold as either an add-on to an existing system that uses ultrasound, optical or radio techniques or as a stand-alone system. The areas of application include geological surveying or detection of flows and mixing in industrial processes.

The invention claimed is:

1. A method of taking electrical impedance tomography measurements while conducting simultaneous wide-band spectroscopy using multiple electrodes located at selected positions external to a volume of a subject body being a part of a human body, comprising simultaneously introducing multiple, original signals by way of selected different electrodes, the original signals being orthogonal or near-orthogonal signals, recording or determining resultant predetermined responses at receiving electrodes, encoding the original signals using a technique of code division multiplexing, de-multiplexing signals received at each receiving electrode and cross-correlating the signals received with the original signals to determine a contribution of each original signal to a composite received signal.

2. The method as claimed in claim 1 in which each original signal is a specific length sequence of pulses with each sequence coded with a channel-specific code.

3. The method as claimed in claim 2 in which the original signals assume a form of pseudorandom noise (PRN) sequences.

4. The method as claimed in claim 1 in which the original signals are broad band codes embracing a frequency spectrum of from 10 Hz to at least 5 MHz.

5. The method as claimed in claim 1 in which the part of the human body is a human head.

6. The method as claimed in claim 5 in which the method includes the step of creating tomographic images indicative of an aneurysm or a stroke.

7. A method of conducting electrical impedance tomography spectroscopy that includes the method of taking electrical impedance tomography measurements as claimed in claim 1 and processing them to produce required spectra.

8. An apparatus for conducting the method as claimed in claim 1 comprising a signal generator for simultaneously producing a set of orthogonal or near-orthogonal signal currents encoded using a technique of code division multiplexing, a set of EIT electrodes connected to apply the signal currents to a body being investigated and to receive compound signal currents applied by way of other electrodes, and computer means programmed to de-multiplex and cross-correlate received signals, process the signals and generate required EIT data or EITS data, or EIT data and EITS data.

9. The apparatus as claimed in claim 8 further including a transformer coupling interposed between a signal generator and each pair of electrodes associated with a particular signal current with a primary winding of each transformer being connected to be energized by the signal generator and a secondary winding of each transformer being connected in series with a resistor between members of a pair of electrodes.

* * * * *